United States Patent

Koike et al.

[11] Patent Number: 5,814,068
[45] Date of Patent: Sep. 29, 1998

[54] SUTURE THREAD FOR INTRACARDIAC SUTURE OPERATION

[75] Inventors: Kazuyuki Koike, Tokyo-to; Yoshikazu Kishigami; Katsuya Miyagawa, both of Ohtsu; Syu Kurashima, Shiga-ken, all of Japan

[73] Assignee: Nissho Corporation, Osaka-fu, Japan

[21] Appl. No.: 874,734

[22] Filed: Jun. 13, 1997

[30] Foreign Application Priority Data

Jun. 20, 1996 [JP] Japan .................................. 8-159471

[51] Int. Cl.$^6$ ...................................................... A61B 17/04
[52] U.S. Cl. .......................... 606/228; 606/148; 606/151
[58] Field of Search .................................. 606/103, 113, 606/157, 151, 228, 213, 232, 148

[56] References Cited

U.S. PATENT DOCUMENTS 4,950,285  8/1990  Wilk .

FOREIGN PATENT DOCUMENTS 0 362113   4/1990  European Pat. Off. .
0 769272   4/1997  European Pat. Off. .
5237128A   9/1993  Japan .
09108228A  4/1997  Japan .
93 13712   7/1993  WIPO .

*Primary Examiner*—Michael Powell Buiz
*Assistant Examiner*—Julian W. Woo
*Attorney, Agent, or Firm*—Birch, Stewart, Kolasch & Birch LLP

[57] ABSTRACT

A suture thread for intracardiac suture operation, comprises a thread guide element (1) and a thread (2) joined to a rear end thereof, the thread guide element (1) being composed of a slender straight member (11) of a super-elastic alloy wire and a looped member (12) of a super-elastic alloy wire provided at a front end of the straight member (11). The thread guide element (1) may be further provided at its rear end with a looped member (13) of a super-elastic alloy wire. The super-elastic alloy may be an alloy selected from the group consisting of Ti-Ni, Cu-Zn-Al and Cu-Al-Ni alloys. The looped member (12) of the suture thread is captured by suture-hooking means (42) of a catheter assembly (C) including a hooking catheter (4).

3 Claims, 3 Drawing Sheets

SUTURE THREAD FOR INTRACARDIAC SUTURE OPERATION

TECHNICAL FIELD OF THE INVENTION

The present invention relates to a suture thread for intracardiac suture operation and, more particularly, to a suture thread for use in performing direct suture of cardiac diseases such as atrial septal defects (ASD), ventricular septal defects (VSD), patent ductus arteriosus (PDA), etc. by intracardiac catheterization involving the insertion of an intracardiac surgical suture instrument into the heart through a peripheral blood vessel.

BACKGROUND OF THE INVENTION

In general, congenital cardiac diseases such as ASD have been treated by surgical operation. As a matter of course, such a surgical operation includes not only treatment of the affected part but also thoracotomy or laparotomy and causes a lot of damage to a patient. In particular, it causes serious damage to children's patients who are poor in physical strength.

Recently, there has been developed a non-surgical procedure, known as a percutaneous transluminal therapeutic catheterization, of occluding atrial septal defects by transvascularly inserting a cardiocatheter into the heart. In 1976, King and Mill have reported the first clinical success of such a procedure. In the procedure employed by King and Mill, an atrial septal defect is occluded by introducing a pair of umbrella-like members into the atrium with an insertion tool composed of a double-layered catheter and a core wire arranged therein, placing said members on opposite sides of the defect, and locking them together at a central hub which crosses the defect.

However, this procedure requires use of a very large-sized insertion tool and hard umbrella-like members, thus making it impossible to apply it to children, especially, to preschool children. As a result of miniaturization of the instrument, Rashkind has developed an occlusion plug of a single umbrella type having a hook and a clinical success of its application to a child has been reported in 1977. However, this procedure includes such a disadvantage that the plug may be hooked on an unintended site of the heart since the plug is provided with the hook. Once the umbrella-like member is opened, it is impossible to relocate the hooked member as well as to draw back the plug from the heart. This requires emergent surgical operation when the plug is hooked on the unintended site of the heart. In order to overcome such a disadvantage, Rashkind has further developed an improved plug comprising two umbrella-shaped occluders having eight stainless struts and being connectable to each other. Nowadays, the plugs of this type has been put into practical use widely to perform occlusion of patent ductus arteriosus.

On the other hand, Japanese patent unexamined publication No. 5-237128 filed by James E. Lock et al discloses an intraatrial occlusion plug comprising two umbrella-shaped members composed of eight stainless steel struts like as the Rashkind's plug, each strut being provided at a central part thereof with a spring coil. This occlusion plug is firmly fixed to the thin intraatrial septum by closely adhering two umbrella-shaped members to each other in the overlapping state. This occlusion plug is called as a clam shell-shaped intraatrial occluder because of its configuration similar to that of a clam being a bivalve. The procedure is carried out by inserting an elongated sheath with a thickness of 11 French through the femoral vein. The occlusion plugs have been widely used in percutaneous transluminal therapeutic catheterization for occlusion of atrial septal defects since such plugs can be applied to patients with a weight of 8 Kg and above.

However, there is a limit to the application of these occlusion plugs since the procedure requires use of the occlusion plugs with a uniform shape for various configurations of atrial septal defects and since the occlusion of a defective opening or hole requires use of an occlusion plug which is twice the size of the defective opening or hole. Thus, the occlusion plugs of the prior art can be applied only to a relatively small defective openings or holes present in the central part of the atrioventricular septum. In addition, there is a fear of evil effects due to use of occlusion plugs since there is no data on long-term use of the occlusion plug left in the heart.

To solve the problems mentioned above, the inventors have developed a catheter assembly for intracardiac suture as disclosed in Japanese patent unexamined publication JP-A-7-269916. The catheter assembly comprises a hooking catheter bent at a distal portion thereof and provided at its distal end with suture-hooking means and at its proximal end with a manipulating element; a first sheath having a lumen for movably holding said hooking catheter therein, said first catheter being bent at a distal portion thereof at the same angle as the hooking catheter; a piercing catheter having a lumen for movably holding said first sheath, the piercing catheter being provided at a distal end with a piercing needle and at the proximal end with a hemostatic means; and a second sheath having a lumen for movably holding said piercing catheter, the second sheath being provided with a hemostatic means at a proximal end thereof, the piercing catheter and second sheath being provided at each distal portion thereof with a side hole for extrusion of said first sheath so that said side hole of said piercing catheter is laid to lie the side hole of said second sheath to allow the first sheath to protrude therethrough when the piercing catheter is inserted into the second sheath until the tip of the piercing needle has reached to the tip of the second sheath.

This catheter assembly for intracardiac suture makes it possible to perform non-surgical occlusion of the atrial septal defect with ease and correctness. However, it is difficult to perform intracardiac suture procedure within the beating heart even if radiopaque suture threads are used for visual inspection of the suture thread site and the needle. Thus, the intracardiac suture procedure requires a skilled person. That is, since the suture thread is lashed within the beating heart because of its softness, it is difficult to observe the situation of the suture thread and it is in danger of the thread getting tangled during the suture procedure. Although the general suture threads are suited for ligation or fixing because of their poor lubricating property, they are hard to pass through the organization as well as to allow its knot to be sent into the organization.

SUMMARY OF THE INVENTION

It is therefore an object of the present invention to provide a suture thread which makes it possible to perform intracardiac suture procedure easily and smoothly.

The above and other objects are achieved by providing a guide element on a thread. According to the present invention, there is provided a suture thread for intracardiac suture operation, which comprises a thread guide element and a thread joined to a rear end thereof, said thread guide element being composed of a slender straight member of a super-elastic alloy wire and a looped member of a super-elastic alloy wire provided at a front end of the straight member, said straight member having the outermost layer of a coating of a lubricating material.

The thread guide element may be further provided at its rear end with a looped member of a super-elastic alloy wire, to which a suture thread may be attached. As the super-elastic alloy, it is preferred to use an alloy selected from the group consisting of Ti-Ni, Cu-Zn-Al and Cu-Al-Ni alloys.

The above and other objects and features of the present invention will become clear from the following description taken in conjunction with a preferred embodiment thereof with reference to the accompanying drawings which are given by way of illustration only, and thus are not limitative of the present invention.

DETAILED DESCRIPTION OF THE PREFERRED EMBODIMENTS

Figure 1:
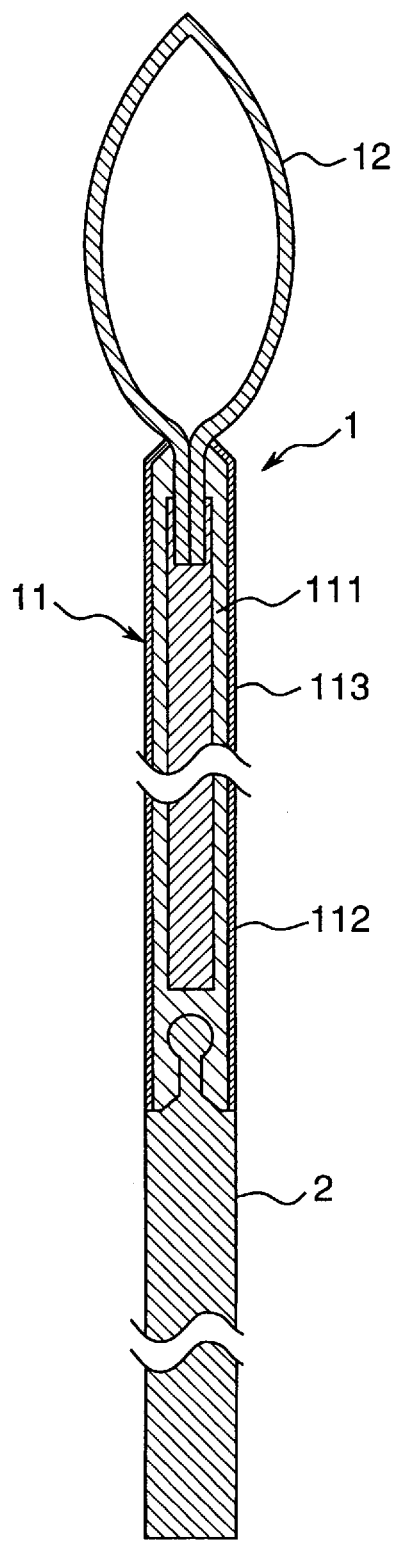
FIG. 1 is a longitudinal cross-sectional view of a suture thread embodying the present invention.
Figure 3:
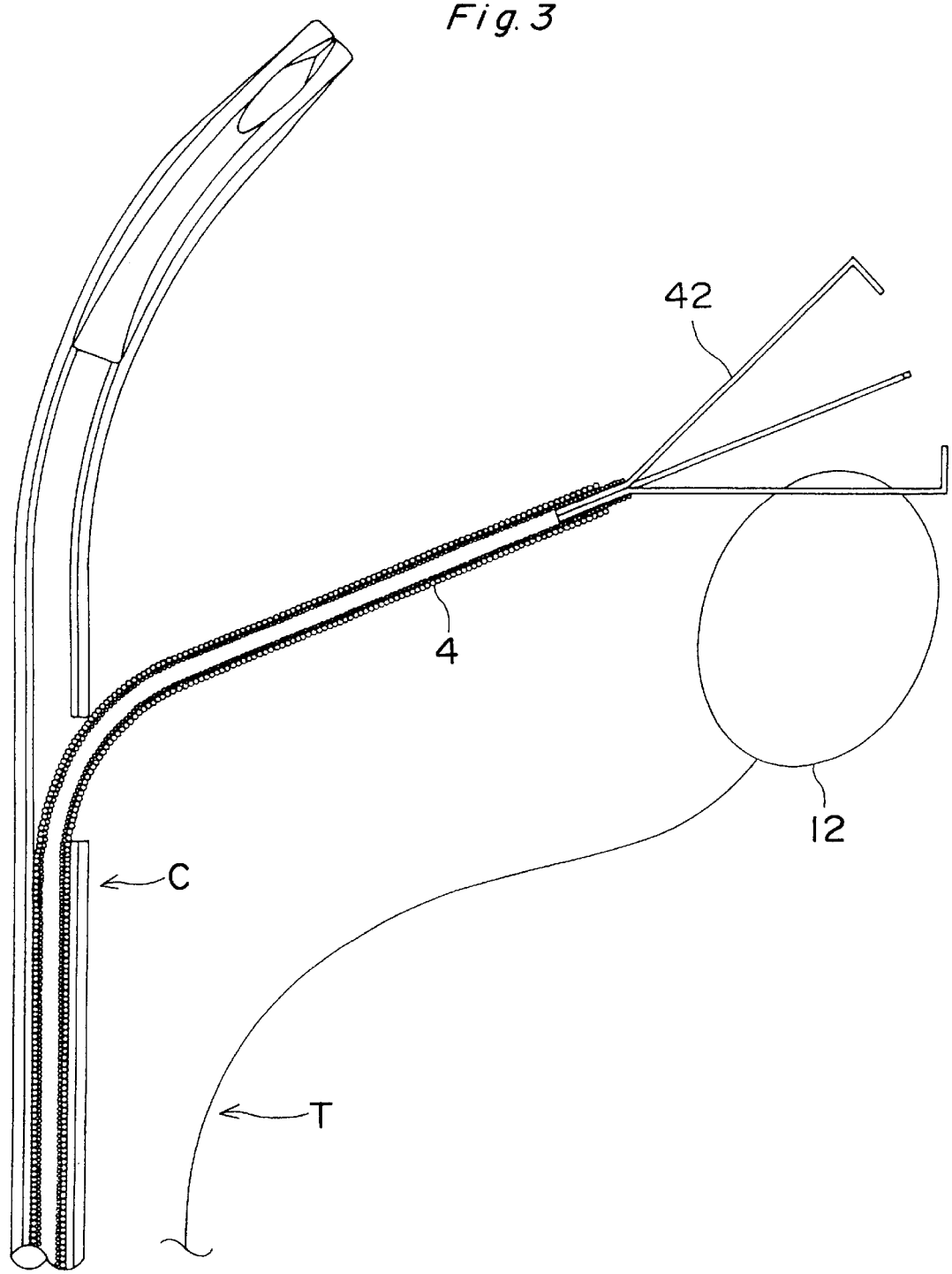
FIG. 3 is an elevational view illustrating a suture thread of FIG. 1 in use.

Referring now to FIG. 1, there is shown a suture thread for intracardiac suture operation of the present invention, which comprises a thread guide element 1 and a thread 2 joined to a rear end of the guide element 1. The suture thread is captured by a catheter assembly C for intracardiac suture procedure, as shown in FIG. 3. The catheter assembly C includes a hooking catheter 4 provided at its distal end with suture-hooking means 42 which captures the looped member 12 joined to the rear end of the thread guide element 1.

The guide element 1, used for guiding the thread 2 to the surgical site of suture, includes a slender straight member 11 of a super-elastic alloy wire and a looped member 12 of a super-elastic alloy wire fixed to a front end of the straight member 11. Preferably, the straight member 11 is composed of a core wire 111 of a super-elastic alloy, a resin layer 112 of a synthetic resin formed on the core wire 111 by coating, and a lubricating layer 113 of a lubricating material formed on the resin layer 112 by coating. If the outermost layer 113 of the straight member 11 is of a lubricating material, there is no need to provide an intermediate resin layer 112 between the core wire 11 and the lubricating layer 113. However, it is preferred to provide the resin layer 112 on the core wire 111 to join the looped members 12 or 13 to the straight member 11 as well as to fix the thread 2 to the guide element 1.

The core wire 111 of the straight member 11 and looped members 12, 13 are made of a super-elastic alloy which is hard to cause plastic deformation. Preferred super-elastic alloys are titanium-nickel (Ti-Ni) alloys, copper-zinc-aluminum (Cu-Zn-Al) alloys, and copper-aluminum-nickel (Cu-Al-Ni) alloys. Preferred lubricating materials for the lubricating layer 113 include dimethyl acrylamide, polyvinyl pyrrolidone and the like. The synthetic resin used for forming the resin layer 112 includes ethylene-vinyl acetate copolymer, polyurethane and the like.

The looped member 12 is made of a super-elastic alloy wire with a diameter of from 0.05 to 1 mm, preferably, from 0.1 to 0.3 mm and formed into an ellipse shape with a longitudinal diameter of 5 to 30 mm, preferably, 10 to 20 mm. This looped member 12 is fixed to the front end of the straight member 11 by physical means, for example, by adhesion, welding or press-fitting, as shown in FIG. 1. Since the looped member 12 is made of a super-elastic alloy wire with a very fine diameter, it transforms freely and makes it easy to insert the thread guide element 1 into a sheath (not illustrated in the drawings) when inserting the thread guide element 1 into the sheath of the catheter.

The straight member 11 includes a core wire 111 with a diameter of from 0.1 to 1.5 mm, preferably, from 0.25 to 0.35 mm and a length of 500 to 3000 mm, preferably, 1000 to 2000 mm.

Figure 2:
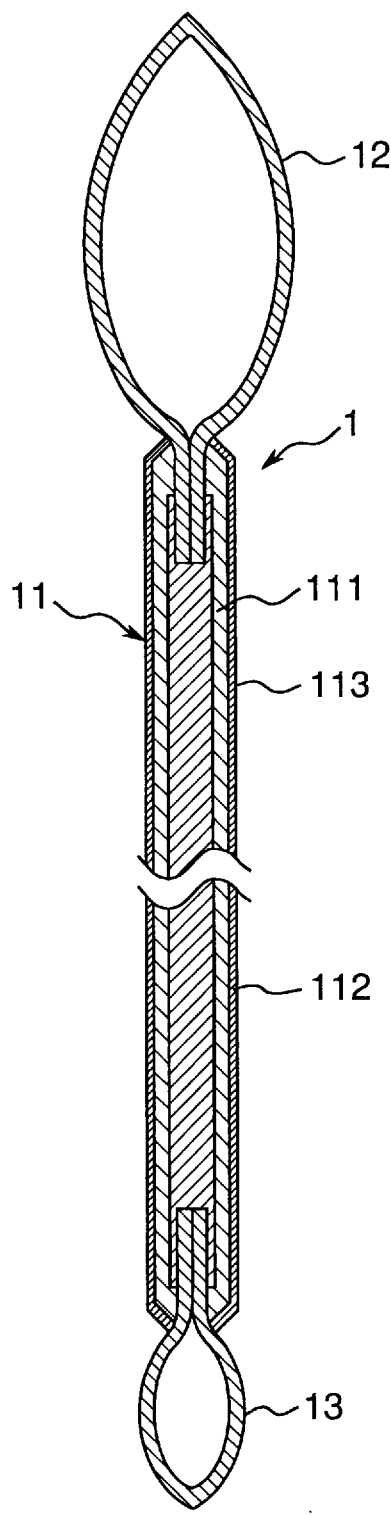
FIG. 2 is a longitudinal cross-sectional view of a suture guide element illustrating another embodiment of the present invention.

In the embodiment of FIG. 1, the thread guide element 1 is composed of a slender straight member 11, a looped member 12 fixed to its front end, a thread 2 jointed to the rear end of the straight member 11. However, the thread guide element 1 may further includes an additional looped member 13 provided on the rear end of the wire 11, as illustrated in FIG. 2. In this case, the thread 2 is fixed to the additional looped member 13 physically or chemically.

The additional looped member 13 is generally made of a super-elastic alloy wire having a diameter of from 0.05 to 1 mm, preferably, from 0.1 to 0.3 mm, and formed into an ellipse shape with a longitudinal diameter of 2 to 20 mm, preferably, 5 to 10 mm. This looped member 13 is fixed to the rear end of the straight member 11 by adhesion, welding or press-fitting, as shown in FIG. 2. Preferred thickness of the lubricating layer 113 ranges from 0.001 to 0.01 mm.

The thread 2 is generally made of synthetic resin such as polypropylene and joined to the rear end or additional looped member of the guide element 1.

Since the suture thread for intracardiac suture procedure of the present invention includes the thread guide element made of a super-elastic alloy at the tip, the suture thread can be seen more easily through a fluoroscope as compared with the conventional radiopaque suture thread, thus making it easy to sequentially displace the thread across the defect. Further, the guide element has super-elasticity and slipping property, there is no fear of entwining which may occur frequently in the conventional suture thread. In addition, the thread permits smooth suture procedure because of its good slipping property.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

We claim:

1. A suture thread for intracardiac suture operation, which comprises a thread guide element and a thread joined to a rear end thereof, said thread guide element being composed of a slender straight member of a super-elastic alloy wire and a looped member of a super-elastic alloy wire provided at a front end of the straight member, said straight member having the outermost layer of a coating of a lubricating material.

2. The suture thread according to claim 1, wherein said tread guide element is further provided at its rear end with an additional looped member of a super-elastic alloy wire, and wherein said thread is joined to said additional looped member.

3. The suture thread according to claim 1, wherein said super-elastic alloy wire is made of an alloy selected from the group consisting of Ti-Ni, Cu-Zn-Al and Cu-Al-Ni alloys.

* * * * *